United States Patent
Dobrinsky et al.

(10) Patent No.: US 10,675,370 B2
(45) Date of Patent: *Jun. 9, 2020

(54) DIFFUSIVE LIGHT ILLUMINATOR

(71) Applicant: Sensor Electronic Technology, Inc., Columbia, SC (US)

(72) Inventors: Alexander Dobrinsky, Silver Spring, MD (US); Michael Shur, Vienna, VA (US); Remigijus Gaska, Columbia, SC (US)

(73) Assignee: Sensor Electronic Technology, Inc., Columbia, SC (US)

(*) Notice: Subject to any disclaimer, the term of this patent is extended or adjusted under 35 U.S.C. 154(b) by 110 days.

This patent is subject to a terminal disclaimer.

(21) Appl. No.: 15/856,649

(22) Filed: Dec. 28, 2017

(65) Prior Publication Data

US 2018/0117195 A1    May 3, 2018

Related U.S. Application Data

(63) Continuation of application No. 14/853,075, filed on Sep. 14, 2015, now Pat. No. 9,855,352.

(Continued)

(51) Int. Cl.
*G02B 6/00* (2006.01)
*A61L 2/10* (2006.01)
(Continued)

(52) U.S. Cl.
CPC ............. *A61L 2/10* (2013.01); *A61L 2/00* (2013.01); *A61L 9/00* (2013.01); *F21V 7/0091* (2013.01);
(Continued)

(58) Field of Classification Search
CPC ..... A61L 2/10; A61L 2/00; A61L 9/00; A61L 2/088; A61L 2209/11; F21V 7/0091;
(Continued)

(56) References Cited

U.S. PATENT DOCUMENTS 4,045,119 A    8/1977  Eastgate
5,675,689 A   10/1997  Nath
(Continued)

FOREIGN PATENT DOCUMENTS

WO    2005011753 A1    2/2005

OTHER PUBLICATIONS

Deo, D., U.S. Appl. No. 15/387, 592, Notice of Allowance, dated Jan. 22, 2018, 37 pages.
(Continued)

*Primary Examiner* — Bao Q Truong
(74) *Attorney, Agent, or Firm* — LaBatt, LLC

(57) ABSTRACT

A diffusive illuminator is provided. The diffusive illuminator includes a set of light sources and a light guiding structure including a plurality of layers. At least some of the layers can be formed of a fluoropolymer and at least one layer can be formed of a transparent fluid. The light guiding structure also includes an emission surface through which diffused light exits. The light guiding structure can further include diffusive elements associated with at least one of the plurality of layers. Each diffusive element can diffuse the light to within forty percent of Lambertian distribution. The diffusive elements can be arranged based on a desired uniformity of the diffused light at a target distance corresponding to a surface to be illuminated. The diffusive illuminator can emit ultraviolet light, and can be implemented as part of a disinfection system.

20 Claims, 10 Drawing Sheets

Related U.S. Application Data

(60) Provisional application No. 62/050,331, filed on Sep. 15, 2014, provisional application No. 62/050,126, filed on Sep. 13, 2014.

(51) Int. Cl.
| | |
|---|---|
| *F21V 7/00* | (2006.01) |
| *F21V 8/00* | (2006.01) |
| *A61L 2/00* | (2006.01) |
| *A61L 9/00* | (2006.01) |
| *A61L 2/08* | (2006.01) |

(52) U.S. Cl.
CPC .............. *G02B 6/00* (2013.01); *G02B 6/0003* (2013.01); *G02B 6/006* (2013.01); *G02B 6/0051* (2013.01); *A61L 2/088* (2013.01); *A61L 2209/11* (2013.01)

(58) Field of Classification Search
CPC ... F21V 2200/00; F21V 2200/20; G02B 6/00; G02B 6/0003; G02B 6/0051; G02B 6/006; G02B 6/0075; G02B 6/0076; G02B 6/0011
See application file for complete search history.

(56) References Cited

U.S. PATENT DOCUMENTS

| | | | |
|---|---|---|---|
| 5,896,483 A | 4/1999 | Wojcik et al. | |
| 6,163,641 A | 12/2000 | Eastgate | |
| 6,314,226 B1 | 11/2001 | Nath | |
| 6,314,227 B1 | 11/2001 | Nath | |
| 6,418,257 B1 | 7/2002 | Nath | |
| 6,468,428 B1 | 10/2002 | Nishii et al. | |
| 6,476,409 B2 | 11/2002 | Iwasaki et al. | |
| 6,501,893 B1 | 12/2002 | Iimura | |
| 6,560,038 B1 * | 5/2003 | Parkyn, Jr. ................. | F21V 5/04 359/726 |
| 6,771,866 B2 | 8/2004 | Iimura | |
| 6,773,584 B2 | 8/2004 | Saccomanno | |
| 6,863,428 B2 | 3/2005 | Lundin | |
| 6,936,854 B2 | 8/2005 | Iwasaki et al. | |
| 7,016,566 B2 | 3/2006 | Dimas et al. | |
| 7,211,763 B2 | 5/2007 | Zhang | |
| 7,613,378 B2 | 11/2009 | Girardon et al. | |
| 7,660,509 B2 | 2/2010 | Bryan et al. | |
| 7,914,852 B2 | 3/2011 | Belz et al. | |
| 7,960,706 B2 | 6/2011 | Ullman | |
| 8,177,383 B2 | 5/2012 | Reuben | |
| 8,434,909 B2 | 5/2013 | Nichol et al. | |
| 8,442,602 B2 | 5/2013 | Wong et al. | |
| 9,061,082 B2 | 6/2015 | Gaska et al. | |
| 9,625,372 B2 | 4/2017 | Bilenko et al. | |
| 9,687,577 B2 | 6/2017 | Dobrinsky et al. | |
| 9,696,484 B2 * | 7/2017 | Dobrinsky ........... | G02B 6/1221 |
| 9,700,655 B2 | 7/2017 | Laudenslager et al. | |
| 9,703,055 B2 | 7/2017 | Dobrinsky et al. | |
| 9,855,352 B2 * | 1/2018 | Dobrinsky ................ | A61L 2/10 |
| 10,442,704 B2 | 10/2019 | Bilenko et al. | |
| 2003/0044149 A1 | 3/2003 | Fraval et al. | |
| 2004/0036560 A1 | 2/2004 | Higuchi et al. | |
| 2006/0002675 A1 | 1/2006 | Choi et al. | |
| 2007/0279935 A1 | 12/2007 | Gardiner et al. | |
| 2009/0034236 A1 | 2/2009 | Reuben | |
| 2010/0014027 A1 | 1/2010 | Li et al. | |
| 2010/0165621 A1 * | 7/2010 | Hoffend, Jr. ......... | G02B 6/0031 362/235 |
| 2011/0149201 A1 | 6/2011 | Powell et al. | |
| 2011/0273906 A1 | 11/2011 | Nichol et al. | |
| 2011/0286222 A1 * | 11/2011 | Coleman ............ | B29D 11/0073 362/326 |
| 2011/0309032 A1 | 12/2011 | Makl | |
| 2013/0106918 A1 | 5/2013 | Bita et al. | |
| 2013/0336839 A1 | 12/2013 | Gil et al. | |
| 2014/0001374 A1 | 1/2014 | Ullman | |
| 2014/0071142 A1 | 3/2014 | Steyn | |
| 2014/0204320 A1 | 7/2014 | Yang et al. | |
| 2014/0332674 A1 | 11/2014 | Goto et al. | |
| 2014/0373606 A1 | 12/2014 | Kraiczek et al. | |
| 2015/0069265 A1 | 3/2015 | Smetona et al. | |
| 2015/0091043 A1 | 4/2015 | Shur et al. | |
| 2015/0360606 A1 | 12/2015 | Thompson et al. | |
| 2016/0074548 A1 | 3/2016 | Dobrinsky et al. | |
| 2017/0097466 A1 | 4/2017 | Dobrinsky et al. | |
| 2017/0290937 A1 | 10/2017 | Dobrinsky et al. | |
| 2017/0299826 A1 | 10/2017 | Dobrinsky et al. | |
| 2018/0095264 A1 | 4/2018 | Borthakur et al. | |

OTHER PUBLICATIONS

Wong, T., U.S. Appl. No. 16/035,749, Final Office Action 1, dated Jan. 10, 2019, 9 pages.
Bedtelyon, J., U.S. Appl. No. 15/854,332, Office Action1, dated May 11, 2018, 26 pages.
Wong, T., U.S. Appl. No. 16/035,749, Notice of Allowance, dated Jul. 30, 2019, 8 pages.
Ippolito, N., U.S. Appl. No. 15/633,118, Notice of Allowance, dated Jan. 24, 2019, 8 pages.
Ippolito, N., U.S. Appl. No. 15/633,118, Office Action 1, dated Sep. 25, 2018, 11 pages.
Bedtelyon,J., U.S. Appl. No. 15/854,332, Notice of Allowance, dated Sep. 26, 2018, 8 pages.
Dobrinsky, A., U.S. Appl. No. 16/035,749, Office Action1, dated Aug. 16, 2018, 11 pages.
Agilent Technologies, "Light Guide Techniques Using LED Lamps, Application Brief I-003," 2001, 22 pages.
Colombe, Y., et al., "Single-mode optical fiber for high-power, low-loss UV transmission," Optics Express, Aug. 2014, p. 19783, vol. 22, No. 16.
Dupont, "Amorphous Fluoroplastic Resin," www.teflon.com/industrial, 2013, 4 pages.
Fevrier, S., et al., "Ultraviolet guiding hollow-core photonic crystal fiber," 2009, 2888-2890, Opt. Lett.34(19).
Gebert, F., et al., "Damage-free single-mode transmission of deep-UV light in hollow-core PCF," Optics Express, Jun. 2014, p. 15388, vol. 22, No. 13.
Gonschior, C. P., et al. "Characterization of UV single-mode and low-mode fibers," 2010, Proc. of SPIE vol. 7559 75590X-1.
Gore® Diffuse Reflector Product, printed from http://www.gore.com/en_xx/products/electronic/specialty/specialty. html?RDCT=gore.com on Sep. 5, 2014.
Joo, B., et al., "Design guidance of backlight optic for improvement of the brightness in the conventional edge-lit LCD backlight," 2010, 6 pages.
Li, C., et al., "Prism-pattern design of an LCD light guide plate using a neural-network optical model," 2010, 5 pages.
Martin, et al., "Ordered arrays of polymeric nanopores by using inverse nanostructured PTFE surfaces," 2012, 10 pages, IOP Publishing.
Yamamoto, N., "Single-mode delivery of 250 nm light using a large mode area photonic crystal fiber," 2009, p. 16933-16940, Opt. Express17(19).
Yang, M., et al., "Optical properties of Teflon AF amorphous fluoropolymers," Jul.-Sep. 2008, 9 pages.
Deo, D., U.S. Appl. No. 14/853,057, Notice of Allowance, dated Mar. 1, 2017, 9 pages.
Deo, D., U.S. Appl. No. 14/853,057, Notice of Allowance, dated Dec. 28, 2016, 15 pages.
Deo, D., U.S. Appl. No. 14/853,057, Office Action1, dated Jul. 21, 2016, 21 pages.
Bedtelyon, J., U.S. Appl. No. 15/633,103, Notice of Allowance, dated Nov. 30, 2017, 5 pages.
Bedtelyon, J., U.S. Appl. No. 15/633,103, Ex Parte Quayle Action, dated Oct. 6, 2017, 15 pages.
Bedtelyon, J., U.S. Appl. No. 14/853,014, Notice of Allowance, dated Feb. 28, 2017, 5 pages.

(56) References Cited

OTHER PUBLICATIONS

Bedtelyon, J., U.S. Appl. No. 14/853,014, Notice of Allowance, dated Nov. 21, 2016, 13 pages.
Bedtelyon, J., U.S. Appl. No. 14/853,014, Office Action1, dated Jul. 1, 2016, 19 pages.
Ippolito, U.S. Appl. No. 14/853,036, Notice of Allowance, dated Mar. 1, 2017, 13 pages.
Ippolito, U.S. Appl. No. 14/853,036, Notice of Allowance, dated Jan. 23, 2017, 18 pages.
Ippolito, U.S. Appl. No. 14/853,036, Office Action1, dated Sep. 14, 2016, 15 pages.
Truong, B., U.S. Appl. No. 14/853,075, Notice of Allowance, dated Aug. 22, 2017, 32 pages.
Kang, S. International Application No. US2015/049917, International Search Report and Written Opinion, dated Dec. 23, 2015, 13 pages.
International Application No. US2015/049922, International Search Report and Written Opinion, dated Mar. 18, 2016, 14 pages.
Deo, D., U.S. Appl. No. 15/387,592, Notice of Allowance2, dated Mar. 5, 2018, 12 pages.

* cited by examiner

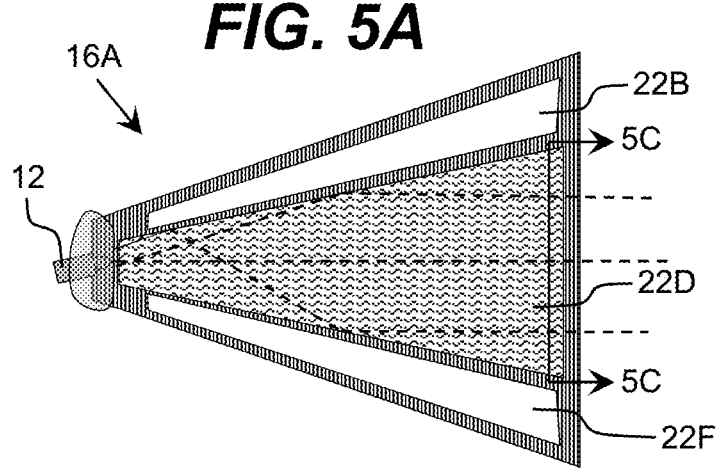
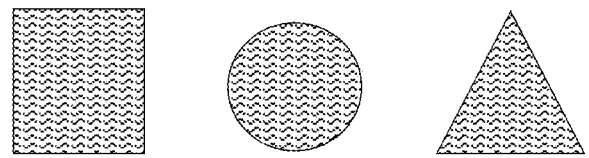
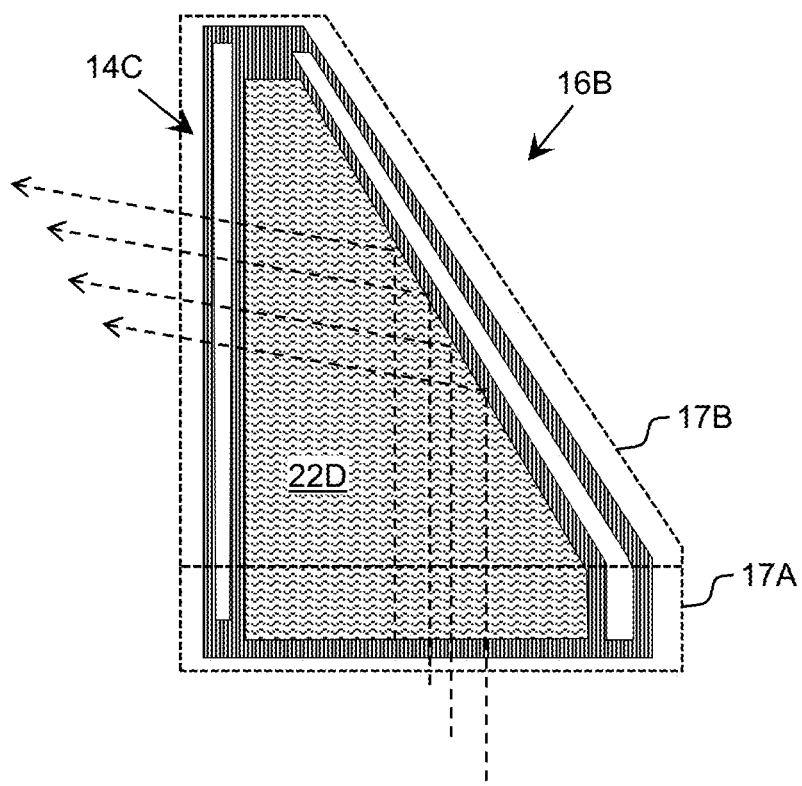

DIFFUSIVE LIGHT ILLUMINATOR

REFERENCE TO RELATED APPLICATIONS

The current application is a continuation of U.S. patent application Ser. No. 14/853,075, filed on 14 Sep. 2015, which claims the benefit of U.S. Provisional Application No. 62/050,126, filed on 13 Sep. 2014, and U.S. Provisional Application No. 62/050,331, filed on 15 Sep. 2014, each of which is hereby incorporated by reference. Aspects of the invention are related to U.S. patent application Ser. No. 14/478,266, which is hereby incorporated by reference.

TECHNICAL FIELD

The disclosure relates generally to ultraviolet radiation, and more particularly, to a solution for generating diffusive ultraviolet radiation.

BACKGROUND ART

The use of light diffusers is common in backlight illumination, which is frequently found in liquid crystal displays (LCDs). For visible light, the criterion of diffuser design is significantly different than that for ultraviolet (UV) radiation. This is largely related to the fact that UV transparent materials are harder to manufacture than corresponding materials for visible light. Further, the transparency of UV materials is typically inferior to the transparency of materials to visible light. In addition, the UV transparent materials are expensive compared to materials transparent to visible light.

Recently, various improvements to backlight visible light illumination design have been proposed. For example, collimating multi-layer optical film (CMOF) provides a cost efficient light management for LCD backlights with integrated optical films. These films provide diffusive capability to LCD backlight illuminators. CMOF is based on multi-layer optical film technology that is used to make current display films, such as dual brightness enhancement film (DBEF), reflective polarizers, and enhanced specular reflector (ESR) films. The CMOFs are used in a new backlight architecture developed by 3M™ and branded as Air Guide. CMOF technology combines two types of nanotechnologies: nanolayer optics and ultra-low refractive index nanofoam. The CMOF film is attached directly to the LCD panel, replacing several separate films used in current light emitting diode (LED) backlight designs. The new design uses a hollow cavity with no free-floating films and no solid light guide. In the Air Guide design, light is spread through the air of the cavity between the LCD panel and the highly reflective film. FIGS. 1A and 1B illustrate the schematics of a previous LED backlight design and 3M's Air Guide design, respectively.

Another traditional design for diffusive wave guiding is shown in FIGS. 2A and 2B. In this design, the LED lights are positioned at a side of the diffuser (see FIG. 2B, for example). The diffuser is composed of several layers: a sheet with micro-features, reflecting and light guiding sheets, and a diffusive sheet followed by optional prismatic and other diffusive sheets. For success of such a design, good light reflective and light transparent materials have to be employed, which is difficult to achieve for ultraviolet illumination.

Currently, UV devices capable of operating to sterilize mobile phones are available, such as the UV Sterilizer for iPhone from Sinco-Elec. Co. This UV sterilizer is a desktop unit that allows a user to place a mobile phone into the sterilizer for about five minutes for UV sterilization. The device turns a blue LED on to indicate the sterilization is in process. Completion of the sterilization process is indicated by the blue indicator LED turning off. The device does not utilize low voltage light emitting diodes and cannot be used as a carry-case.

SUMMARY OF THE INVENTION

Aspects of the invention provide a diffusive illuminator. The diffusive illuminator includes a set of light sources and a light guiding structure including a plurality of layers. At least some of the layers can be formed of a fluoropolymer and at least one layer can be formed of a transparent fluid. The light guiding structure also includes an emission surface through which diffused light exits. The light guiding structure can further include diffusive elements associated with at least one of the plurality of layers. Each diffusive element can diffuse the light within forty percent of Lambertian distribution. The diffusive elements can be arranged based on a desired uniformity of the diffused light at a target distance corresponding to a surface to be illuminated. The diffusive illuminator can emit ultraviolet light, and can be implemented as part of a disinfection system.

A first aspect of the invention provides a diffusive illuminator comprising: a set of light sources; a light guiding structure including a plurality of layers, wherein the light guiding structure includes a plurality of layers formed of a fluoropolymer and at least one layer formed of a transparent fluid, and wherein the light guiding structure includes an emission surface through which diffused light exits; and a plurality of diffusive elements associated with at least one of the plurality of layers, wherein each of the plurality of diffusive elements diffuses the light to within forty percent of Lambertian distribution, and wherein the plurality of diffusive elements are arranged based on a desired uniformity of the diffused light at a target distance corresponding to a surface to be illuminated.

A second aspect of the invention provides a system comprising: a diffusive illuminator including: a set of light sources; a light guiding structure including a plurality of layers, wherein the light guiding structure includes a plurality of layers formed of a fluoropolymer and at least one layer formed of a transparent fluid, and wherein the light guiding structure includes an emission surface through which diffused light exits; and a plurality of diffusive elements associated with at least one of the plurality of layers, wherein each of the plurality of diffusive elements diffuses the light to within forty percent of Lambertian distribution, and wherein the plurality of diffusive elements are arranged based on a desired uniformity of the diffused light at a target distance corresponding to a surface to be illuminated; and means for adjusting the plurality of diffusive elements based on at least one attribute of the diffused light.

A third aspect of the invention provides a disinfection system comprising: a diffusive illuminator including: a set of ultraviolet light sources; a light guiding structure including a plurality of layers, wherein the light guiding structure includes a plurality of layers formed of a fluoropolymer and at least one layer formed of an ultraviolet transparent fluid, and wherein the light guiding structure includes an emission surface through which diffused ultraviolet light exits; and a plurality of diffusive elements associated with at least one of the plurality of layers, wherein each of the plurality of diffusive elements diffuses the ultraviolet light to within forty percent of Lambertian distribution, and wherein the plurality of diffusive elements are arranged based on a desired uniformity of the diffused ultraviolet light at a target distance corresponding to a surface to be illuminated; and a control system configured to operate the set of ultraviolet light sources to disinfect an item using the diffused ultraviolet light.

The illustrative aspects of the invention are designed to solve one or more of the problems herein described and/or one or more other problems not discussed.

BRIEF DESCRIPTION OF THE DRAWINGS

These and other features of the disclosure will be more readily understood from the following detailed description of the various aspects of the invention taken in conjunction with the accompanying drawings that depict various aspects of the invention.

FIGS. 5A and 5B show illustrative light guiding structures according to embodiments, while FIG. 5C shows illustrative cross-sections of the light guiding structures according to embodiments.

FIG. 6A shows an illustrative light guiding structure including a brightness enhancing film according to an embodiment, while

It is noted that the drawings may not be to scale. The drawings are intended to depict only typical aspects of the invention, and therefore should not be considered as limiting the scope of the invention. In the drawings, like numbering represents like elements between the drawings.

DETAILED DESCRIPTION OF THE INVENTION

Figure 1A:
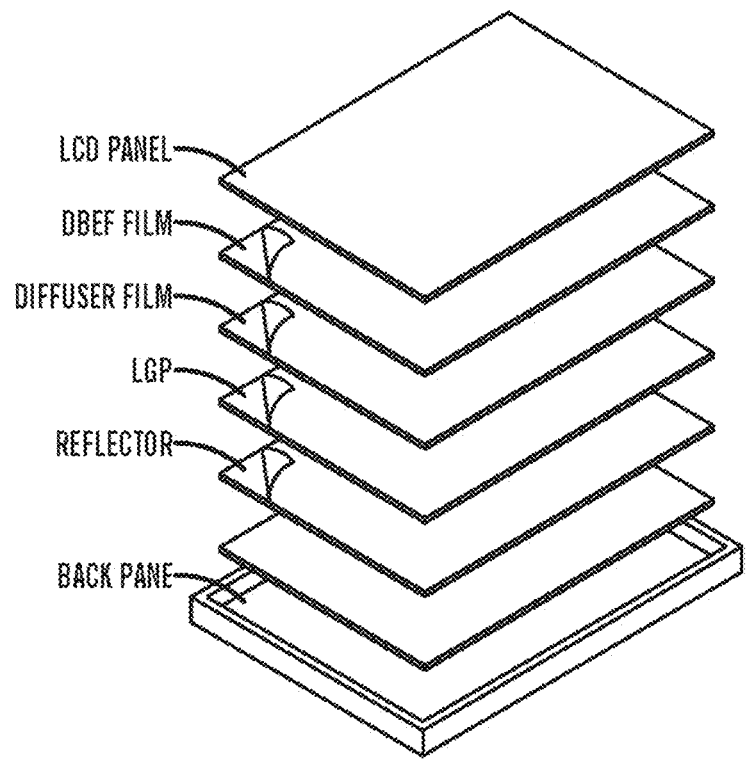
FIGS. 1A and 1B illustrate the schematics of a previous LED backlight design and 3M's Air Guide design, respectively.

As indicated above, aspects of the invention provide a diffusive illuminator. The diffusive illuminator includes a set of light sources and a light guiding structure including a plurality of layers. At least some of the layers can be formed of a fluoropolymer and at least one layer can be formed of a transparent fluid. The light guiding structure also includes an emission surface through which diffused light exits. The light guiding structure can further include diffusive elements associated with at least one of the plurality of layers. Each diffusive element can diffuse the light to within forty percent of Lambertian distribution. The diffusive elements can be arranged based on a desired uniformity of the diffused light at a target distance corresponding to a surface to be illuminated. The diffusive illuminator can emit ultraviolet light, and can be implemented as part of a disinfection system.

As used herein, unless otherwise noted, the term "set" means one or more (i.e., at least one) and the phrase "any solution" means any now known or later developed solution. Furthermore, as used herein, ultraviolet radiation/light means electromagnetic radiation having a wavelength ranging from approximately 10 nanometers (nm) to approximately 400 nm, while ultraviolet-C (UV-C) means electromagnetic radiation having a wavelength ranging from approximately 100 nm to approximately 280 nm, ultraviolet-B (UV-B) means electromagnetic radiation having a wavelength ranging from approximately 280 to approximately 315 nanometers, and ultraviolet-A (UV-A) means electromagnetic radiation having a wavelength ranging from approximately 315 to approximately 400 nanometers. As also used herein, a material/structure is considered to be "reflective" to ultraviolet light of a particular wavelength when the material/structure has an ultraviolet reflection coefficient of at least thirty percent for the ultraviolet light of the particular wavelength and is highly reflective when the material/structure has an ultraviolet reflection coefficient of at least seventy percent. Furthermore, a material/structure is considered to be "transparent" to ultraviolet light of a particular wavelength when the material/structure allows at least ten percent of the ultraviolet light, which is radiated at a normal incidence to an interface of the layer, to pass there through; highly transparent when at least thirty percent of the radiation passes there through; and substantially transparent when at least eighty percent of the radiation passes there through.

As used herein, the term "disinfection" and its related terms means treating a product, device, food item, and/or the like, hereinafter "the item," so that it includes a sufficiently low number of contaminants (e.g., chemical) and microorganisms (e.g., virus, bacteria, and/or the like) and can be handled as part of a desired human interaction with no or no reasonable risk for the transmission of a disease or other harm to the human. For example, disinfection of the item means that the item has a sufficiently low level of active microorganisms and/or concentration of other contaminants that a typical human can interact with the item without suffering adverse effects from the microorganisms and/or contaminants present on the item. In addition, disinfection can include sterilization. As used herein, the term "sterilization" and its related terms means neutralizing an ability of a microorganism to reproduce, which may be accomplished without physically destroying the microorganism. In this example, a level of microorganisms present on the item cannot increase to a dangerous level and will eventually be reduced, since the replication ability has been neutralized. A target level of microorganisms and/or contaminants can be defined, for example, by a standards setting organization, such as a governmental organization.

Figure 3A:
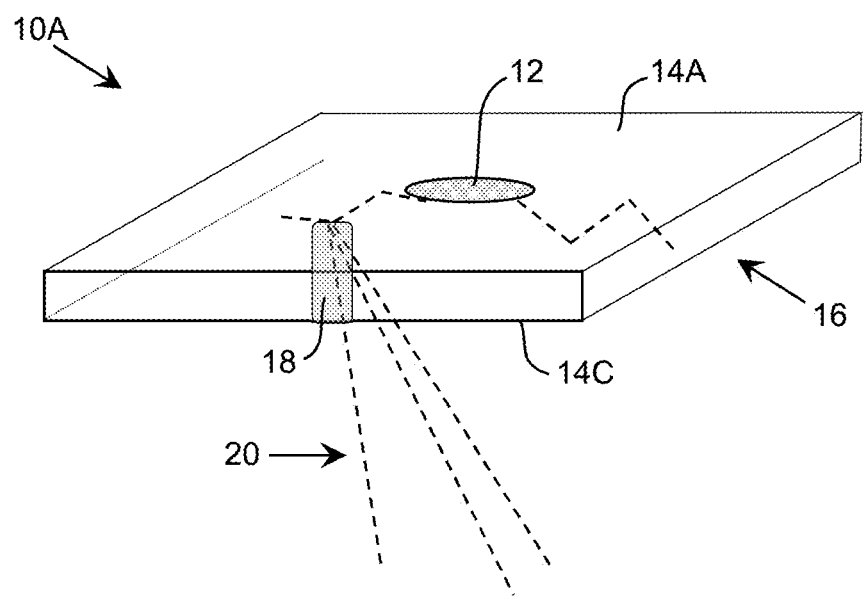
FIGS. 3A and 3B show schematics of illustrative diffusive illuminators according to embodiments.
Figure 3B:
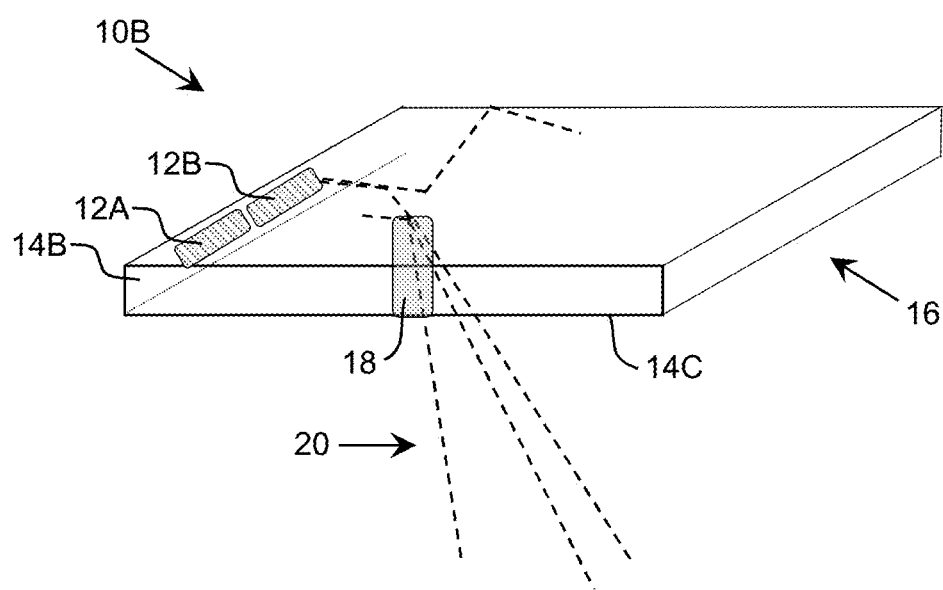

Turning to the drawings, FIGS. 3A and 3B show schematics of illustrative diffusive illuminators 10A, 10B, respectively, according to embodiments. Each diffusive illuminator 10A, 10B is shown including a set of light sources 12. In the diffusive illuminator 10A, a single light source 12 is shown located adjacent to a back (top) surface 14A of the diffusive illuminator 10A. In the diffusive illuminator 10B, two light sources 12A, 12B are shown located adjacent to a side surface 14B of the diffusive illuminator 10B, resulting in an edge emitting diffusive illuminator 10B. However, it is understood that these configurations are only illustrative, and a diffusive illuminator 10A, 10B can include any configuration of one or more light sources 12 located adjacent to any combination of one or more of the various surfaces of the diffusive illuminator 10A, 10B.

Regardless, during operation of the diffusive illuminator 10A, 10B, diffusive light 20 is emitted from an emission (bottom) surface 14C of the diffusive illuminator 10A, 10B. To this extent, each diffusive illuminator 10A, 10B can include a light guiding structure 16 and a set of diffusive elements 18. Each diffusive element 18 can be associated with (e.g., located within, located on, extend from, and/or the like) at least one layer in the light guiding structure, and be configured to diffuse light emitted by the corresponding set of light sources 12 and guided by the light guiding structure 16. The light guiding structure 16 and diffusive element(s) 18 can operate cooperatively to result in diffusive light 20 being emitted from a large surface area of the bottom surface 14C. While the diffusive illuminators 10A, 10B are shown having a rectangular cuboid shape, it is understood that this is only illustrative, and a diffusive illuminator 10A, 10B can have any desired shape.

In an embodiment, the diffusive illuminator 10A, 10B can be configured to emit diffusive ultraviolet radiation 20. To this extent, the set of light sources 12 can comprise any combination of one or more ultraviolet radiation emitters 12. For example, an ultraviolet radiation emitter 12 can comprise a high intensity ultraviolet lamp (e.g., a high intensity mercury lamp), a discharge lamp, an ultraviolet light emitting diode (LED), a super luminescent LED, an ultraviolet laser diode, and/or the like.

Figure 4:
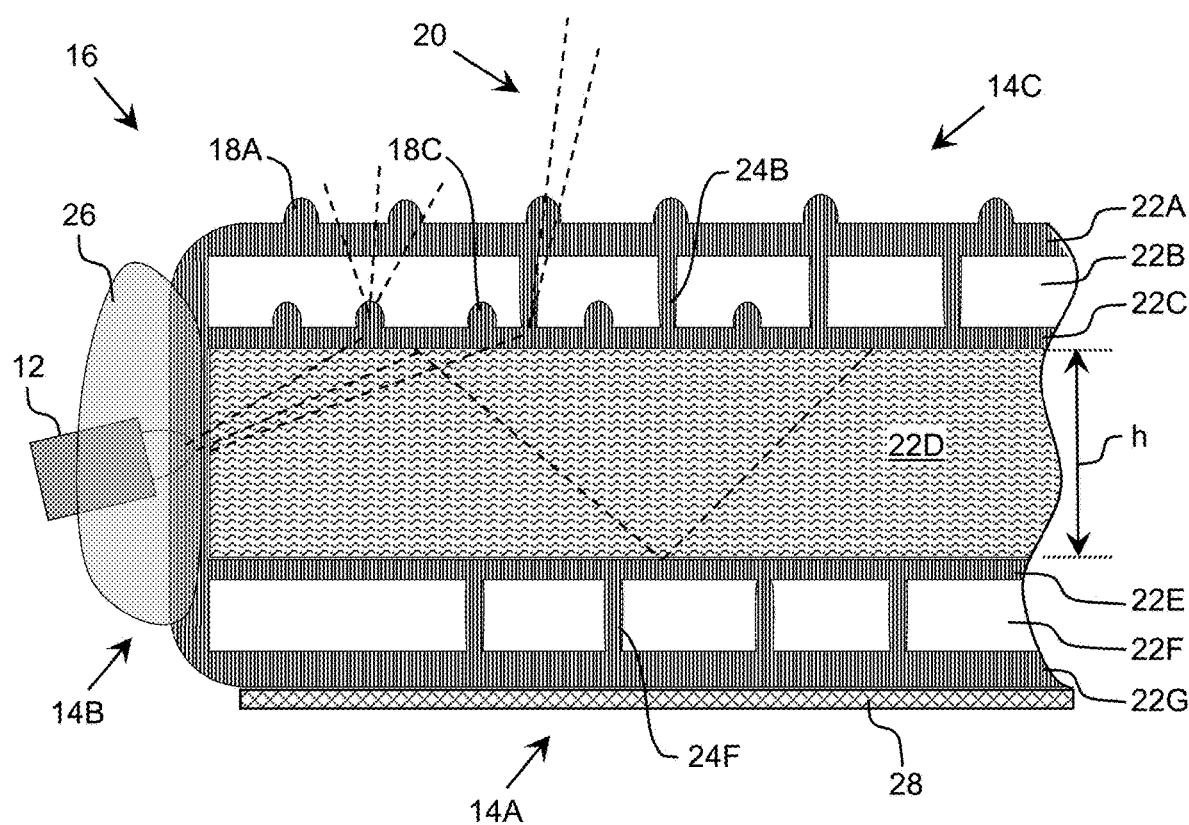
FIG. 4 shows a cross-section of an illustrative light guiding structure according to an embodiment.

In an embodiment, the light guiding structure 16 utilizes total internal reflection (TIR) to propagate the light there through. To this extent, FIG. 4 shows a cross-section of an illustrative light guiding structure 16 according to an embodiment. The light guiding structure 16 includes multiple layers 22A-22G. Layers 22A, 22C, 22E, and 22G can be formed of any suitable type of transparent material. For example, when the radiation is ultraviolet radiation, the material can be an ultraviolet transparent fluoropolymer-based material. Illustrative fluoropolymers capable of being utilized to form the light guiding structure 16 include: fluorinated ethylene-propylene (EFEP), fluorinated ethylene propylene (FEP), perfluoroalkoxy (PFA), tetrafluoroethylene hexafluoropropylene vinylidene fluoride (THV), poly-tetrafluoroethylene (PTFE), polyvinylidene fluoride (PVDF), ethylene-tetrafluoroethylene (ETFE), ethylene chlorotrifluoroethylene (ECTFE), polychlorotrifluoroethene (PCTFE), a copolymer of tetrafluoroethylene and perfluoromethylvinylether (MFA), low density polyethylene (LDPE), perfluoroether (PFA), an amorphous fluoroplastic resin (e.g., Teflon AF 2400), and/or the like. While primarily described in conjunction with fluoropolymers, it is understood that other comparable materials can be utilized. Illustrative materials include polylactide (PLA), fused silica, sapphire, THE, and/or the like.

Each layer 22A, 22C, 22E, 22G can have a thickness, which is sufficiently thin to provide a desired level of transparency. For example, a layer 22A, 22C, 22E, 22G can be formed of Teflon AF 2400 and have a thickness of several micrometers (e.g., ten micrometers or less) or even several tens of micrometers (e.g., forty micrometers or less). An illustrative solution for fabricating such fluoropolymer layers is shown, for example, in U.S. Pat. No. 7,914,852, which is hereby incorporated by reference. Another solution for fabricating a light guiding structure described herein is shown and described in U.S. Provisional Application No. 62/050,126. In an embodiment, the fluoropolymer is applied onto a thin layer of fused silica. In an embodiment, selection of the thicknesses and/or refractive indexes of the materials is performed using a genetic algorithm. In this case, multiple possible combinations of values are evaluated with a subset of the best performing values used, along with some randomness, to create a new group of values to be evaluated. Such a process can be repeated any number of times to arrive at a set of values.

Regardless, the light guiding structure 16 includes layers 22B, 22D, 22F, which are filled with a transparent fluid. In an embodiment, layers 22B, 22F are filled with a transparent gas while the layer 22D is filled with a transparent liquid. In an embodiment, the gas in the layers 22B, 22F can have a low refractive index (e.g., at most ninety percent of the refractive index of the material forming the adjacent layers 22A, 22C, 22E, 22G), such as ambient air. In an embodiment, the liquid in the layer 22D is substantially transparent to ultraviolet radiation. In this case, the liquid has a transparency at least similar (e.g., within ten percent) to the transparency of purified water for light wavelengths in the range of 240 nanometers to 360 nanometers. In an embodiment, the liquid in the layer 22D is purified water as defined by the U.S. Food and Drug Administration. Alternatively, the liquid can be water sufficiently clean for human consumption (potable water).

For a layer 22B, 22F including a gas, the light guiding structure 16 can further include a corresponding set of pillars 24B, 24F. The pillars 24B, 24F also can be formed of a fluoropolymer-based material described herein. The pillars 24B, 24F can be configured to maintain a shape of the corresponding low refractive index guiding layer 22B, 22F, respectively. To this extent, the pillars 24B, 24F can be located in any pattern/random arrangement and can have any combination of one or more sizes and/or shapes, which is suitable for providing a desired amount of support. While not shown, it is understood that any fluid-filled layer, such as the layer 22D, can include a set of pillars. In an embodiment, the pillars 24B, 24F comprise diffusive elements. In this case, as illustrated, the diffusive elements start at one layer, such as the layer 22A, extend through a layer 22B, and end at another layer 22C. When both sets of pillars 24B, 24F are included, the pillars 24B can be staggered in relation to the pillars 24F.

As illustrated, a light source 12 (e.g., an ultraviolet radiation emitter) can be coupled to the light guiding structure 16 at a location adjacent to a side 14B of the light guiding structure 16. The coupling mechanism 26 used to attach the light source 12 to the light guiding structure 16 can be configured to hold the light source 12 in a position such that light enters the light guiding structure 16 at an angle optimal for wave guiding, e.g., at an angle larger than the total internal reflection angle for the light guiding structure 16. In an embodiment, at least thirty percent of the light generated by the light source 12 is guided along the layer 22D. In an embodiment, the coupling mechanism 26 is a domain formed of a fluoropolymer-based material described herein, in which the light source 12 is embedded. While only a single light source 12 is shown, it is understood that any number of light sources 12 can be coupled to the light guiding structure 16 in any of various possible combinations of locations.

One or more layers 22A-22G of the light guiding structure 16 can include a set of diffusive elements associated therewith, which are configured to allow light to propagate through the emission surface 14C out of the light guiding structure 16 in a diffusive manner. For example, the layer 22A is shown including a set of diffusive elements 18A, and the layer 22C is shown including a set of diffusive elements 18C. As illustrated, the diffusive elements 18A can be located on an outer surface of the layer 22A forming the emission surface 14C. Embodiments of diffusive elements 18A, 18C described herein can have any of various shapes including: truncated cone, lens, sphere, pyramid, inverted truncated cone, inverted pyramid, and/or the like. Furthermore, it is understood that a set of diffusive elements 18A, 18C can include a combination of diffusive elements of two or more different shapes. The diffusive elements 18A, 18C can be formed using any solution, such as surface patterning or roughening, welding/fusing the diffusive elements 18A, 18C to the corresponding layer 22A, 22C, and/or the like.

In an embodiment, each diffusive element 18A, 18C is capable of diffusive transmission/reflection of the radiation 20 approximating a Lambertian distribution. In particular, an angular distribution of intensity of radiation 20 transmitted/reflected from the diffusive element 18A, 18C can be normalized by total emitted power and compared to the Lambertian distribution. As used herein, the distribution approximates a Lambertian distribution when the deviation from the Lambertian distribution at each emitted angle is less than forty percent. The distribution substantially approximates a Lambertian distribution when the deviation is less than ten percent from a Lambertian distribution at each emitted angle. Furthermore, a distance between two adjacent diffusive elements 18A, 18C located on a surface can be selected to be smaller than an effective area of a surface illuminated by the diffusive radiation 20 transmitted/reflected by the diffusive elements 18A, 18C. To this extent, the spacing can be determined based on the distribution of the radiation 20 from a diffusive element 18A, 18C as well as a target distance between the diffusive element 18A, 18C and a surface of an object being illuminated. Furthermore, when implemented as part of a disinfection system as described herein, spacing between adjacent diffusive elements 18A, 18C can be determined based on an expected spatial density of contamination on a surface to be disinfected. In this case, the distance can be inversely proportional to the expected spatial density of contamination.

Additionally, one or more of the layers 22A, 22C, 22E, and 22G can be formed of and/or coated with a reflective material. When utilized, a reflective coating can be located over an entirety of the layer 22A, 22C, 22E, and 22G or only a portion of the layer 22A, 22C, 22E, and 22G. Furthermore, the reflective coating can be located on either the outermost or innermost surface of the layer 22A, 22C, 22E, and 22G. For example, the layer 22G is shown including a reflective coating 28 on an outermost surface of the layer 22G. However, it is understood that this is only illustrative. To this extent, depending on the application, any surface of the light guiding structure 16 can contain a reflective coating. The reflective coating can be applied using any solution, such as evaporating a reflective metal (e.g., aluminum), coating with a reflective polymer (e.g., Teflon), and/or the like. In an embodiment, the reflective coating 28 is formed of a highly reflective material, such as highly polished aluminum, and/or the like. In a more particular embodiment, the reflective coating 28 is formed of a diffusively reflective material, such as a highly ultraviolet reflective expanded polytetrafluoroethylene (ePTFE) membrane (e.g., GORE® Diffuse Reflector Material), and/or the like.

In an embodiment, the material forming the reflective coating 28 is selected based on one or more optical characteristics of the light guiding structure 16. For example, the reflective coating 28 can be selected such that the reflectivity of the material is comparable to the transparency of the layers 22A, 22C, 22E, 22G within the light guiding structure 16. Furthermore, the layers 22A, 22C, 22E, 22G can be partially reflective and partially transparent and a small ultraviolet absorption. It is understood that ultraviolet absorption can be minimized, subject to other optimization parameters. Regardless, an ETFE film, such as Fluon® ETFE Film, has as much as ninety percent transmission for ultraviolet rays in the range of 280 nm to 360 nm. In this case, the reflective coating 28 can be formed of a material having a reflectivity of approximately ninety percent (+/− five percent). It is understood that embodiments of a light guiding structure 16 can include various combinations of other devices, which can be used to redirect, diffuse, wave guide, recirculate, and/or the like, the light emitted by the light source 12. Illustrative additional devices include one or more reflectors/mirrors, a reflective/transparent mesh, and/or the like.

A spacing between two or more light sources 12 included in a diffusive illuminator 10A, 10B (FIGS. 3A, 3B) can be determined based on one or more attributes of the light guiding structure 16. For example, for a light ray propagating at the total internal reflection (TIR) angle of approximately fifty degrees, a distance that the light ray propagates within the fluid in the layer 22D of the light guide 16 between collisions with the walls 22C, 22E of the light guiding structure 16 is about 1.2*h, where h is the thickness of the layer 22D of the light guiding structure 16. The light ray will lose approximately fifty percent of its intensity after approximately six collisions with the walls 22C, 22E, which corresponds to an overall lateral distance on the order of 7*h. For retention of at least thirty percent of the intensity, the lateral distance of travel can be as much as 13*h. For example, for a thickness h of one millimeter, a lateral distance of travel of a light ray of approximately 1.3 centimeters will deliver an intensity of about thirty percent for the light propagating at an angle of fifty degrees to a surface normal of the walls 22C, 22E of the light guiding structure 16. Based on a desired intensity and uniformity of the illumination, as well as optical properties of the light guiding structure 16, the spacing between two or more light sources 12 can be readily determined. In an embodiment, a thickness of the layer 22D is at most ten percent of a length of the layer 22D.

Light rays propagating at greater than the TIR angle can travel further while retaining a comparable intensity (due to less frequent collisions with the walls 22C, 22E). In an embodiment, a light source 12 is configured to emit light at least partially collimated in a direction of the light guiding structure 16. In this case, most of the light emitted by the light source 12 will collide with the walls 22C, 22E at angles significantly larger than the TIR angle. At least partial collimation of the light emitted by the light source 12 can be achieved using any solution. For example, the emitting properties of an LED included in the light source 12 can be modified/selected to emit at least partially collimated light (e.g., a laser diode can be utilized), an LED can be combined with a reflector (e.g., parabolic reflector, conic reflector, truncated pyramid reflector, and/or the like) to at least partially collimate the light, and/or the like.

In an embodiment, one or more attributes of the light guiding structure 16 can be configured to increase an angle at which most light emitted by the light source 12 impacts the walls of the light guiding structure 16. For example, one or more regions of the light guiding structure 16 can have a variable diameter and/or cross section. To this extent, FIGS. 5A and 5B show illustrative light guiding structures 16A, 16B, respectively, according to embodiments, while FIG. 5C shows illustrative cross-sections of the light guiding structures according to embodiments. As shown in FIG. 5A, the light guiding structure 16A can have a diameter that continuously increases in a direction away from the light source 12. In an embodiment, each of the fluid-filled layers 22B, 22D, 22F of the light guiding structure 16A can have an increasing diameter. In another embodiment, only the central layer 22D has an increasing diameter. In any event, as illustrated, the increasing diameter of the light guiding structure 16A can result in the light emitted by the light source 12 having an increased collimation, which can result in much longer transmittance of the radiation.

A light guiding structure described herein can have any combination of various attributes. For example, as shown in FIG. 5B, the light guiding structure 16B can include a first region 17A having a substantially constant cross-section and/or diameter, and a second region 17B having a continuously decreasing diameter with respect to the direction of the light. As illustrated, the second region 17B can result in redirection of the radiation propagating through the layer 22D, e.g., resulting in the radiation being emitted from an emission surface 14C of the light guiding structure 16B. In an embodiment, a region 17B having a varying cross-section area can be fabricated from a different material than a material utilized to form a main light guiding region 17A (e.g., which can have a constant cross-section). For example, the varying cross-section area region 17B can be fabricated from a material, such as fused silica, or the like, which has a higher transparency than the material used to form the main light guiding region 17A (e.g., a fluoropolymer). Similarly, as illustrated in FIG. 5C, a light guiding structure described herein can have a cross-section of any shape, such as triangular, rectangular (e.g., square), elliptical (e.g., circular), and/or the like, which can be utilized based on the corresponding application requirements. In an embodiment, the light guiding structure 16A has a prism shape, with the light source 12 coupled to a small area of the prism. In another embodiment, a light guiding structure can have a wedge shape.

Figure 6A:
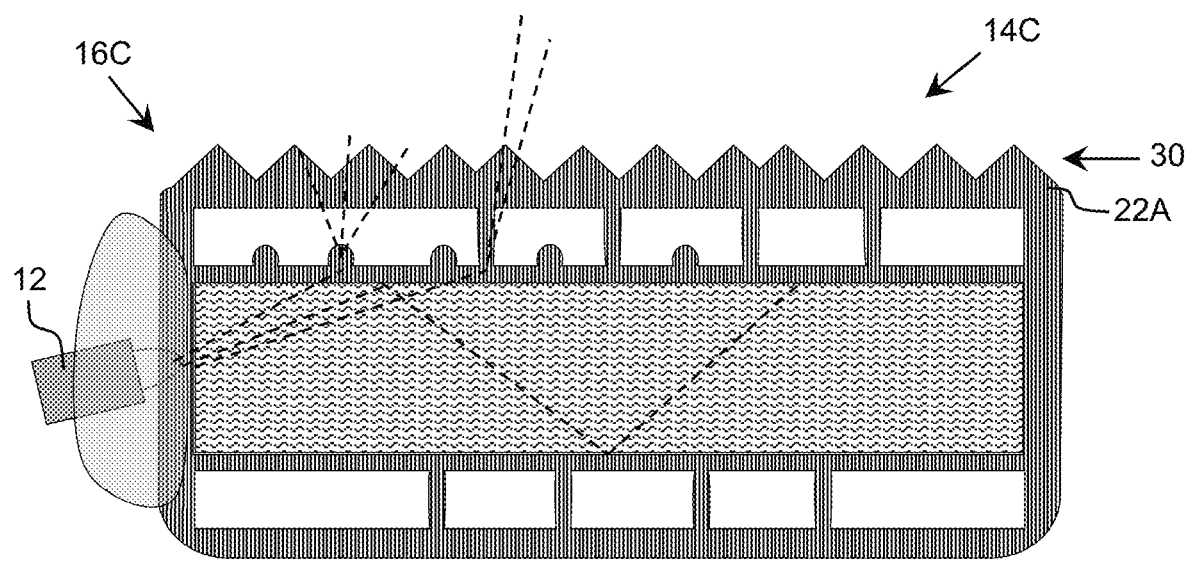
Figure 6B:
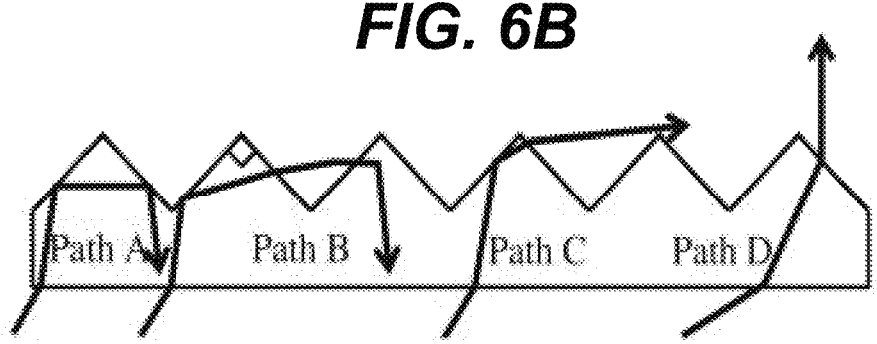
FIGS. 6B and 6C illustrate the effect on the resulting emitted light.
Figure 6C:
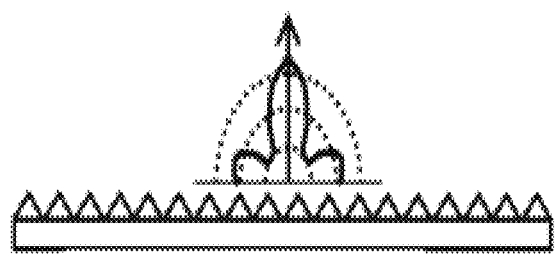

Additionally, a light guiding structure described herein can include one or more layers having a brightness enhancing film. For example, FIG. 6A shows an illustrative light guiding structure 16C including a brightness enhancing film 30 according to an embodiment, while FIGS. 6B and 6C illustrate the effect on the resulting emitted light. In this case, the brightness enhancing film 30 includes a set of prisms located on an outermost surface of the layer 22A, which forms the emission surface 14C of the light guiding structure 16C. The brightness enhancing film 30 can be fabricated using any solution, such as embossing or printing over the layer 22A. As illustrated in FIGS. 6B and 6C, the brightness enhancing film 30 can alter an angular distribution of the emitted radiation. For example, FIG. 6B illustrates illustrative changes in direction of light rays passing through the brightness enhancing film 30, which results in some light rays being recycled back into the light guiding structure 16C. FIG. 6C illustrates an illustrative overall distribution of intensity of the radiation emitted from the light guiding structure 16C.

Figure 7:
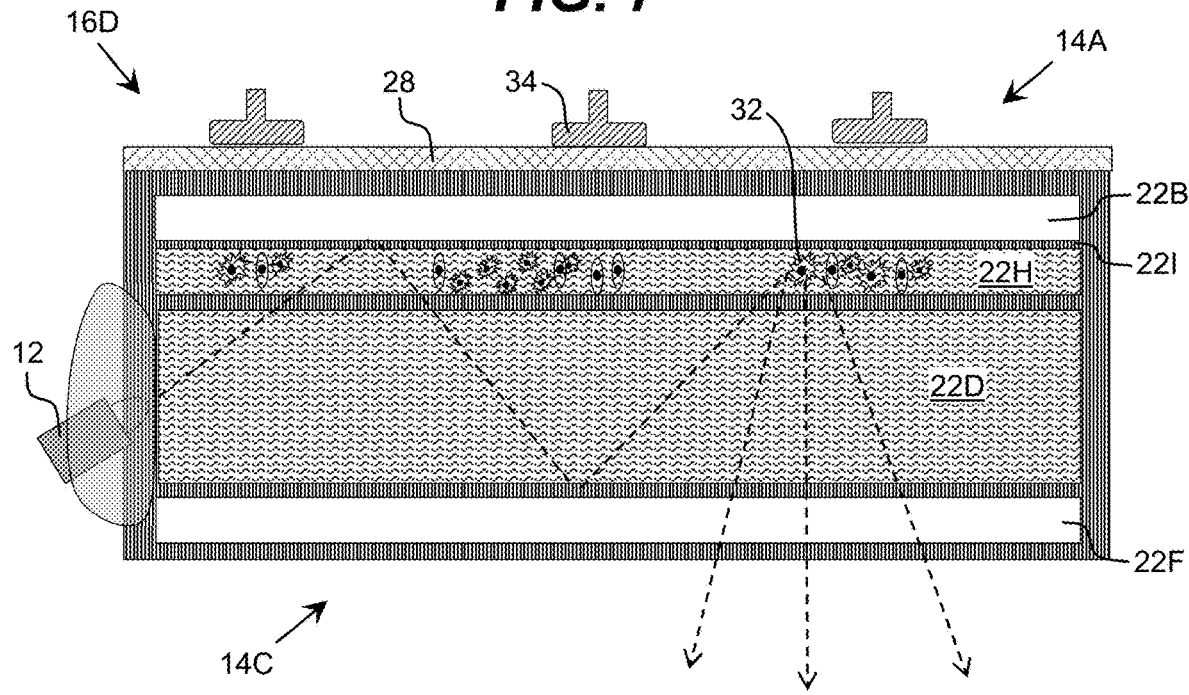
FIG. 7 shows an illustrative light guiding structure according to another embodiment.

A light guiding structure described herein can include various alternative internal configurations of layers and/or features which can be altered. For example, FIG. 7 shows an illustrative light guiding structure 16D according to another embodiment. In this case, the light guiding structure 16D includes a second liquid-filled layer 22H located adjacent to a main liquid-filled layer 22D through which most of the radiation is propagating before being emitted through the emission surface 14C. As illustrated, the second liquid-filled layer 22H can be significantly (e.g., at least approximately four times) thinner than the main liquid-filled layer 22D.

The second liquid-filled layer 22H can include diffusive elements 32. As illustrated, the diffusive elements 32 can be suspended in the liquid, and can move within the second liquid-filled layer 22H. In an embodiment, some or all of the diffusive elements 32 have an elongated shape. The diffusive elements 32 can have differing characteristics (e.g., sizes, shapes, and/or the like). In an embodiment, each diffusive element 32 is capable of diffusive transmission/reflection of the radiation approximating or substantially approximating Lambertian distribution. In an embodiment, diffusive elements 32 can be included within the main liquid-filled layer 22D. To this extent, an embodiment of the light guiding structure can include a liquid-filled layer 22D with diffusive elements 32, without the second liquid-filled layer 22H. In an embodiment, a thickness of a layer, such as the layer 22H, including the diffusive elements 32 is comparable to, but slightly larger than a size of the diffusive elements 32 to enable the diffusive elements 32 to move freely and rotate.

Figure 1B:
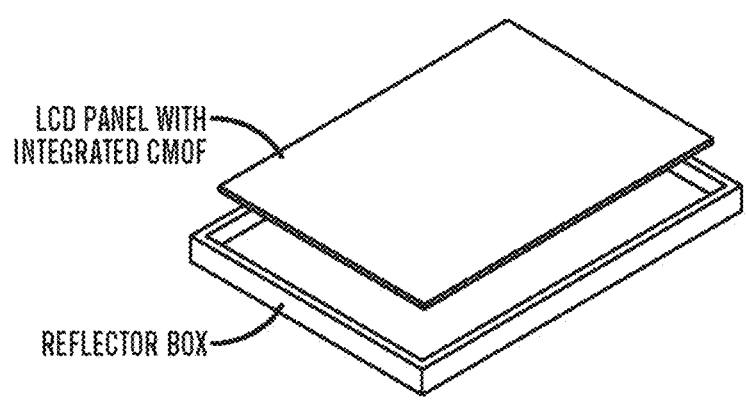
Figure 2A:
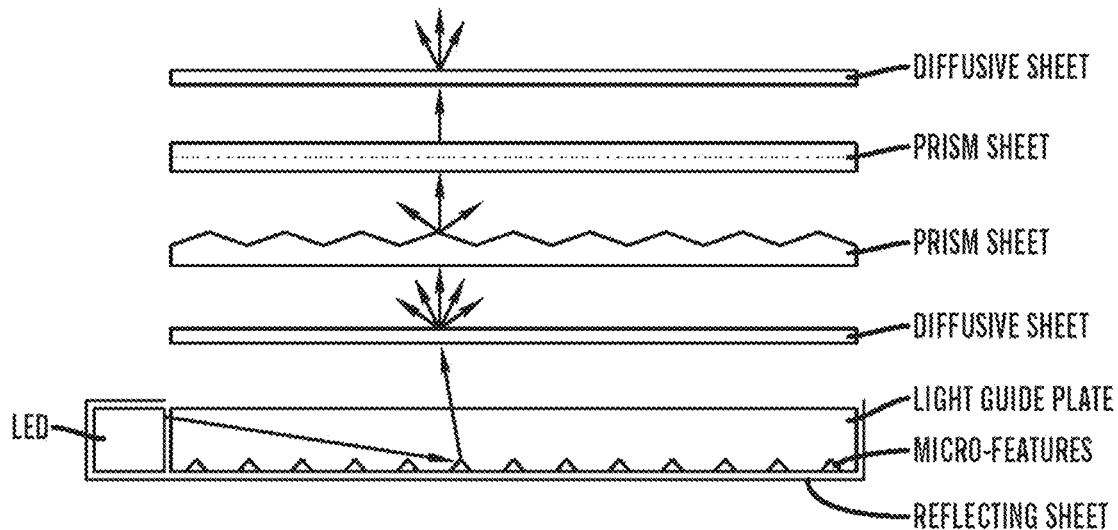
FIGS. 2A and 2B show a diffusive wave guiding design according to the prior art.
Figure 2B:
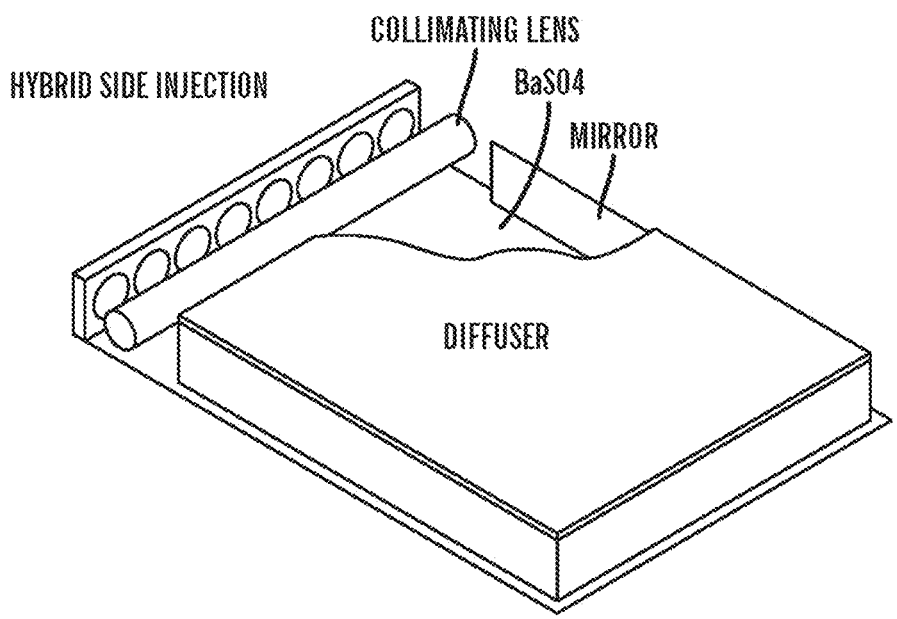

In an embodiment, the light guiding structure 16D is implemented as part of a system (such as a diffusive illuminator 10A, 10B shown in FIGS. 1A and 1B), which includes one or more mechanisms to selectively move the diffusive elements 32. For example, the diffusive elements 32 can be influenced by a magnetic field. In an embodiment, the diffusive elements 32 contain a metal (e.g., magnetic or iron) core, and the system can include a set of magnets 34. A more particular embodiment of a diffusive element 32 includes an iron or magnetic core embedded within an aluminum particle. A still more particular embodiment of a diffusive element 32 includes an iron or magnetic core embedded within an aluminum particle, which is embedded in a fluoropolymer or fused silica shell. The shell of a diffusive element 32 can include one or more features, such as air bubbles, surface roughness, and/or the like, which can increase the diffusive properties of the diffusive element 32. Embodiments include a plurality of diffusive elements 32 including a combination of differing types of diffusive elements described herein.

Regardless, the system can adjust one or more aspects of the magnets 34 to selectively move the diffusive elements 32. For example, the system can include a mechanism (e.g., a mechanical arm and an actuator, a track, and/or the like) for moving the magnets 34 along a back surface 14A of the light guiding structure 16D, which can be covered with a highly reflective film 28. Movement of the magnets 34 can cause the diffusive elements 32 to move due to, for example, magnetic attraction. In this manner, the positioning of the diffusive elements 32 can be selectively altered. Furthermore, an embodiment can enable a strength of the magnetic field affecting the diffusive elements 32 to be varied. For example, embodiments can move the magnets 34 closer to and/or further away from the diffusive elements 32, turn the magnets 34 (e.g., electromagnets) on and off, increase or decrease current applied to the magnets 34, and/or the like, which can result in varying control over the movement of the diffusive elements 32. In an embodiment, a default magnetic field is selected to create friction between the diffusive elements 32 and a wall 22I, which is sufficient to disallow movement of the diffusive elements 32 due to external vibration, e.g., due to rotation or other movement of the light guiding structure 16D.

It is understood that various alternative configurations incorporating particles can be implemented. For example, while not shown, it is understood that a gas-filled layer 22B, 22F, can include diffusive elements 32. Additionally, it is understood that reflective elements can be utilized instead of diffusive elements.

Figure 8:
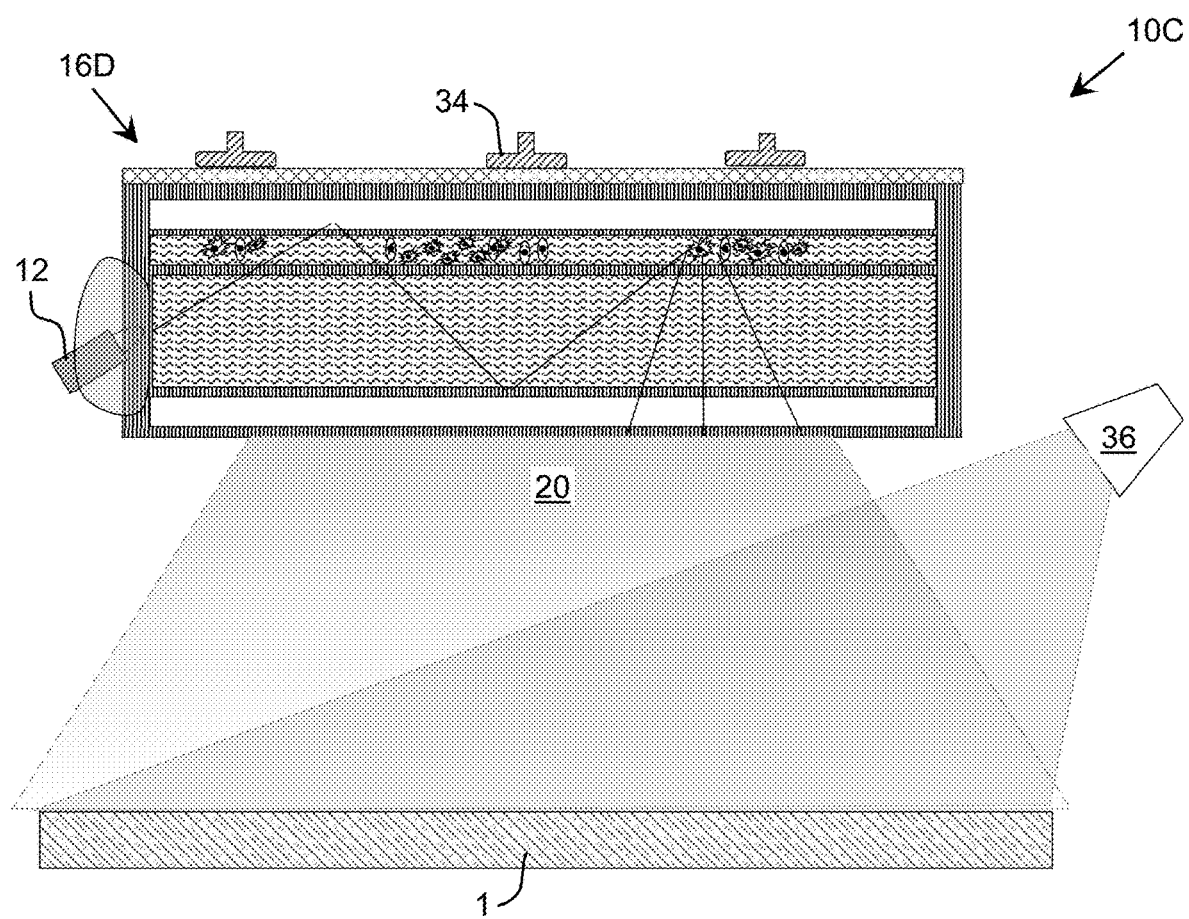
FIG. 8 shows an illustrative system including a light guiding structure according to an embodiment.

FIG. 8 shows an illustrative system 10C including the light guiding structure 16D shown in FIG. 7 according to an embodiment. As discussed, the system 10C can include various components for selectively operating the light source(s) 12 and/or the magnet(s) 34 to cause diffusive radiation (e.g., ultraviolet radiation) 20 to be emitted from the light guiding structure 16D. The radiation 20 can be directed onto a surface of an object 1. Additionally, the system 10C can include a sensing device 36, which can acquire data regarding the radiation 20, which can subsequently be used by a control system to monitor and/or adjust one or more aspects of the operation of the light guiding structure 16D. For example, the sensing device 36 can be a camera, which can acquire data regarding a distribution of the radiation 20 over the surface of the object 1.

In an embodiment, the sensing device 36 is a camera sensitive to ultraviolet radiation. Alternatively, the system can be configured to emit visible radiation 20 (e.g., blue light) concurrent with ultraviolet radiation and/or during a calibration period, which can be sensed by a sensing device 36 sensitive to visible light and can be used to obtain an approximation of the distribution. In another embodiment, a surface of the object 1 can comprise a fluorescent material, which visibly fluoresces when exposed to ultraviolet radiation. In this case, the sensing device 36 can capture the visible fluorescence and derive the distribution of the ultraviolet radiation 20 therefrom. Regardless, a control system can adjust a location and/or strength of one or more of the magnets 34, turn on/off one or more of the light sources 12 and/or magnets 34, and/or the like, based on data acquired by the sensing device 36. In an embodiment, a density of the diffusive elements 32 (FIG. 7) present in a particular location is directly correlated with the intensity of fluorescent emission. Optimization of the distribution of the ultraviolet light can be performed using any solution, such as a genetic algorithm. In this case, the magnets 34 can be placed in various locations and the distribution analyzed. Subsequently, a subset of the various configurations can be used, with randomness, to generate new configurations for analysis. The process can be repeated a desired number of times to arrive at a desired configuration.

A system including a diffusive illuminator (e.g., diffusive ultraviolet illuminator) described herein can be utilize for disinfecting any of various types of items. For example, the system can comprise a device used to disinfect an electronic gadget, a food item, and/or the like. An illuminator described herein can be incorporated with an existing enclosure, and also be configured to disinfect the enclosure (e.g., a cell phone case, a refrigeration system, and/or the like) and/or the item(s) stored in the enclosure. The enclosure can include a rotatable holder for items stored therein, so that the items are thoroughly exposed to the ultraviolet radiation.

Figure 9:
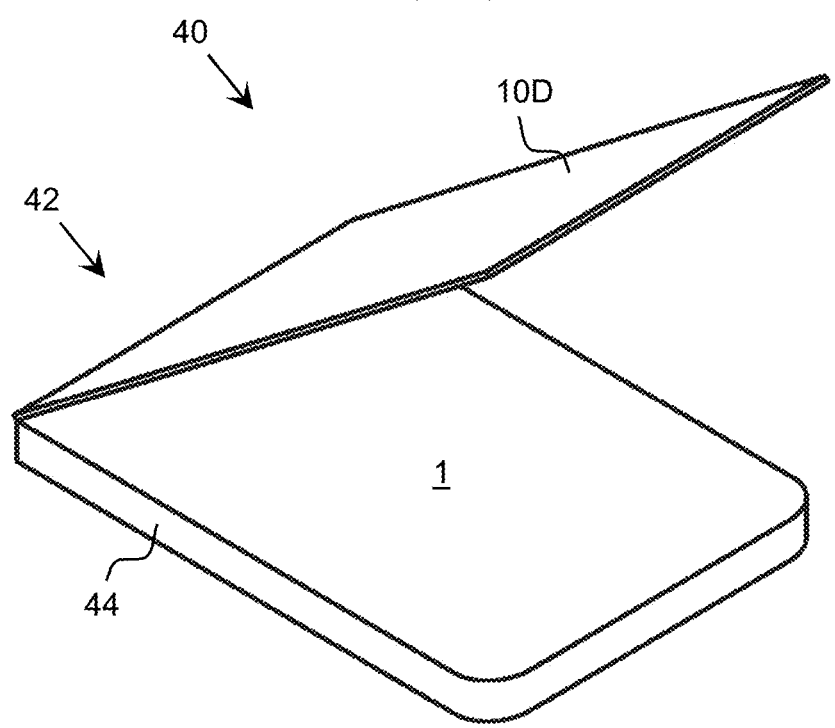
FIG. 9 shows an illustrative UV disinfection system according to an embodiment.

For example, FIG. 9 shows an illustrative UV disinfection system 40 according to an embodiment. The system 40 includes an enclosure 42 including a diffusive UV illuminator 10D, which can be configured as described herein. The UV illuminator 10D can be located on a first side of the enclosure 42, which can be hingedly connected to a second side 44 of the enclosure 42. In an embodiment, the second side 44 of the enclosure includes an electronic gadget 1. The electronic gadget 1 can be permanently or temporarily secured within the second side 44, temporarily placed within the second side 44, and/or the like. Illustrative electronic gadgets 1 include mobile phones, tablets, music players, laptops, keyboards, and/or the like.

During operation, the diffusive UV illuminator 10D is secured to the second side 44 to enable a contaminated surface of the electronic gadget 1 to be disinfected by radiating diffusive UV radiation onto the surface. Furthermore, it is understood that the UV disinfection enclosure 42 can include two or more UV illuminators 10D, each of which is configured to emit diffusive UV radiation directed at a unique surface or a unique portion of a surface of the object 1 to be disinfected. In an embodiment, the remaining interior surfaces of the enclosure 42 can be diffusively reflective of the ultraviolet radiation. Furthermore, the interior surfaces of the enclosure 42 can include a photo-catalyst, which can improve the disinfection. For example, the photo-catalyst can be a layer of titanium dioxide, copper, silver, and/or the like. Regardless, the ultraviolet radiation can be turned off when the two sides 10D, 44 of the enclosure 42 are not secured (e.g., the cover is open) and the interior (e.g., the face of the electronic gadget 1) is exposed. The enclosure 42 also can include a mechanism for ejecting an item (e.g., the electronic gadget 1) when the cover is open. Use of diffusive UV radiation can provide an effective disinfection of an item even with a relatively low power of UV radiation. For example, a substantial reduction of $e.\ coli$ colonies can be achieved by disinfecting for approximately forty minutes using a weak UV radiation of about one microwatt per centimeter squared.

Figure 10:
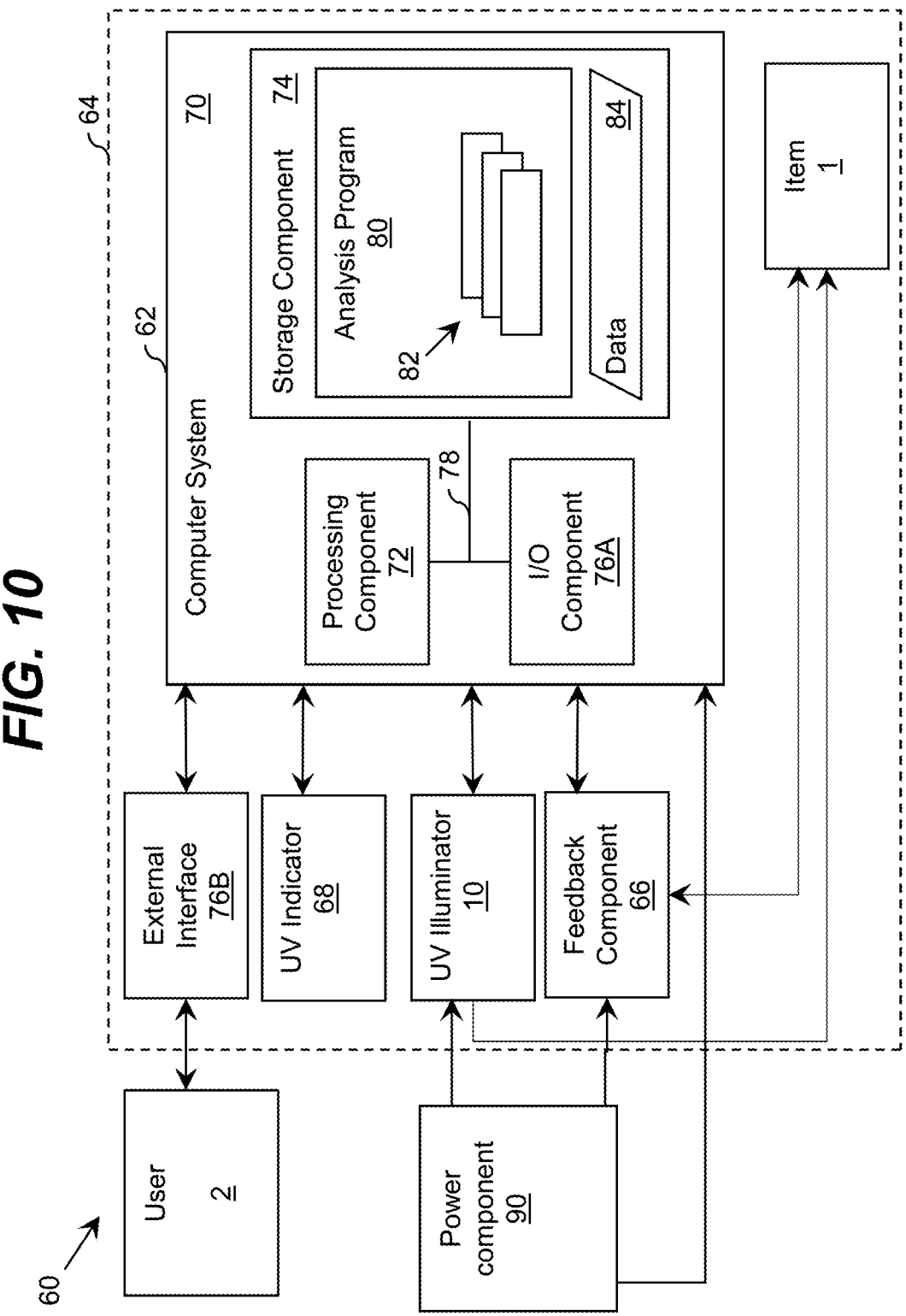
FIG. 10 shows an illustrative ultraviolet radiation system according to an embodiment.

FIG. 10 shows an illustrative ultraviolet radiation system 60 according to an embodiment, which can be utilized to disinfect an item 1. In this case, the system 60 includes a monitoring and/or control system 62, which can be incorporated in a disinfection enclosure 64 and/or located apart from the disinfection enclosure 64. Regardless, the monitoring and/or control system 62 can be implemented as a computer system 70 including an analysis program 80, which makes the computer system 70 operable to manage a diffusive ultraviolet radiation illuminator 10 by performing a process described herein. In particular, the analysis program 80 can enable the computer system 70 to operate the diffusive ultraviolet radiation illuminator 10 to generate and direct ultraviolet radiation toward the item 1 to be disinfected and process data corresponding to one or more attributes regarding the item 1, which is acquired by a feedback component 66, and/or an ultraviolet radiation history stored as data 84.

While a single diffusive ultraviolet radiation illuminator 10 is shown, it is understood that the enclosure 64 can include any number of diffusive ultraviolet radiation illuminators 10, the operation of which the computer system 70 can collectively and/or separately manage using a process described herein. Further, a single diffusive ultraviolet radiation illuminator 10 can include any number of ultraviolet radiation sources. In any case, it is understood that the computer system 70 can individually control each ultraviolet radiation source within the diffusive ultraviolet radiation illuminator 10, each diffusive ultraviolet radiation source, and/or control two or more of the ultraviolet radiation sources as a group.

In an embodiment, during an initial period of operation (e.g., after an item 1 is placed within or attached to the enclosure 64, and/or the like), the computer system 70 can acquire data from the feedback component 66 regarding one or more attributes of the item 1 and generate data 84 for further processing. The data 84 can include a presence of biological activity (e.g., microorganisms, viruses, bacteria, and/or the like) on a surface of the item 1, a usage history of the item 1 (e.g., timestamps for the removal of and relocation of the item 1 in the enclosure 64), a frequency of usage of the item 1, a disinfection schedule history for the item 1, and/or the like. The feedback component 66 can utilize detectors of UV, visible, and/or infrared radiation that can be used to analyze the radiation from the object to determine the data 84 using any solution. The computer system 70 can use the data 84 to control one or more aspects of the ultraviolet radiation generated by the ultraviolet illuminator 10 in order to disinfect the item 1.

Furthermore, one or more aspects of the operation of the ultraviolet radiation source(s) 12 (FIGS. 3A, 3B) within the illuminator 10 can be controlled by a user 1 via an external interface component 76B. The external interface component 76B can be located on an exterior of the enclosure 64 and allow the user 2 to choose when to turn on/off the ultraviolet radiation source (e.g., the illuminator 10). However, it is understood that a sensor and/or switch can determine the presence of the item 1 within the enclosure 64 and that enclosure 64 is closed in order to generate ultraviolet radiation to avoid harming the user 2. The external interface component 76B can include a touch screen that shows control dials for adjusting an intensity, scheduling, and other operational properties of the ultraviolet radiation source(s). In an embodiment, the external interface component 76B can include a keyboard, a plurality of buttons, a joystick-like control mechanism, and/or the like, to control the ultraviolet radiation source(s).

The computer system 70 is shown including a processing component 72 (e.g., one or more processors), a storage component 74 (e.g., a storage hierarchy), an input/output (I/O) component 76A (e.g., one or more I/O interfaces and/or devices), and a communications pathway 78. In general, the processing component 72 executes program code, such as the analysis program 80, which is at least partially fixed in the storage component 74. While executing program code, the processing component 72 can process data, which can result in reading and/or writing transformed data from/to the storage component 74 and/or the I/O component 76A for further processing. The pathway 78 provides a communications link between each of the components in the computer system 70. The I/O component 76A and/or the external interface component 76B can comprise one or more human I/O devices, which enable a human user 2 to interact with the computer system 70 and/or one or more communications devices to enable a system user 2 to communicate with the computer system 70 using any type of communications link. To this extent, during execution by the computer system 70, the analysis program 80 can manage a set of interfaces (e.g., graphical user interface(s), application program interface, and/or the like) that enable human and/or system users 2 to interact with the analysis program 80. Furthermore, the analysis program 80 can manage (e.g., store, retrieve, create, manipulate, organize, present, etc.) the data, such as data 84, using any solution.

In any event, the computer system 70 can comprise one or more general purpose computing articles of manufacture (e.g., computing devices) capable of executing program code, such as the analysis program 80, installed thereon. As used herein, it is understood that "program code" means any collection of instructions, in any language, code or notation, that cause a computing device having an information processing capability to perform a particular function either directly or after any combination of the following: (a) conversion to another language, code or notation; (b) reproduction in a different material form; and/or (c) decompression. To this extent, the analysis program 80 can be embodied as any combination of system software and/or application software.

Furthermore, the analysis program 80 can be implemented using a set of modules 82. In this case, a module 82 can enable the computer system 70 to perform a set of tasks used by the analysis program 80, and can be separately developed and/or implemented apart from other portions of the analysis program 80. When the computer system 70 comprises multiple computing devices, each computing device can have only a portion of the analysis program 80 fixed thereon (e.g., one or more modules 82). However, it is understood that the computer system 70 and the analysis program 80 are only representative of various possible equivalent monitoring and/or control systems 62 that may perform a process described herein. To this extent, in other embodiments, the functionality provided by the computer system 70 and the analysis program 80 can be at least partially implemented by one or more computing devices that include any combination of general and/or specific purpose hardware with or without program code. In each embodiment, the hardware and program code, if included, can be created using standard engineering and programming techniques, respectively. In another embodiment, the monitoring and/or control system 62 can be implemented without any computing device, e.g., using a closed loop circuit implementing a feedback control loop in which the outputs of one or more sensing devices are used as inputs to control the operation of one or more other devices (e.g., LEDs). Illustrative aspects of the invention are further described in conjunction with the computer system 70. However, it is understood that the functionality described in conjunction therewith can be implemented by any type of monitoring and/or control system 62, such as one which can be implemented without any type of computing device.

Regardless, when the computer system 70 includes multiple computing devices, the computing devices can communicate over any type of communications link. Furthermore, while performing a process described herein, the computer system 70 can communicate with one or more other computer systems, such as the user 2, using any type of communications link. In either case, the communications link can comprise any combination of various types of wired and/or wireless links; comprise any combination of one or more types of networks; and/or utilize any combination of various types of transmission techniques and protocols, such as Bluetooth.

The system 60 also can include an ultraviolet radiation indicator 68 (e.g., an LED), which can be operated by the computer system 70 to indicate when ultraviolet radiation is being generated and directed at the item 1 within the enclosure 64. The ultraviolet radiation indicator 68 can include one or more LEDs for emitting a visual light for the user 2.

The computer system 70 is configured to control the UV illuminator 10 to direct diffusive ultraviolet radiation at the item 1. The feedback component 66 is configured to acquire data used to monitor a plurality of attributes regarding the item 1 and/or the ultraviolet radiation emitted by the UV illuminator 10 over a period of time. The feedback component 66 can include a plurality of sensing devices, each of which can acquire data used by the computer system 70 to monitor the set of attributes and/or operation of the UV illuminator 10.

It is understood that the plurality of attributes for the item 1 can include any combination of one or more of: a frequency of the usage of the item 1, a presence of biological activity on the item 1, a usage of the item, a disinfection schedule history for the item 1, and/or the like. In the case of determining usage details for the item 1, a sensing device (feedback component 66) can include a sensor and/or a switch to sense that an item 1 is physically contained within the enclosure 64. Alternatively, the sensor and/or switch can sense that the item 1 is not located within the enclosure 64 and assume that the item 1 is being used.

In the case of determining a presence of biological activity on the item 1, the feedback component 66 can also determine a location of the biological activity, a type of biological activity (e.g., type of organism), a concentration of the biological activity, an estimated amount of time an organism has been in a growth phase (e.g., exponential growth and/or stationary), and/or the like. Furthermore, the feedback component 66 can determine information on the variation of the biological activity over time, such as a growth rate, a rate with which an area including the biological activity is spreading, and/or the like. In an embodiment, a set of biological activity dynamics are related to various attributes of bacteria and/or virus activity on the item 1, including, for example, the presence of detectable bacteria and/or virus activity, measured bacteria and/or virus population/concentration time dynamics, growth phase, and/or the like.

In an embodiment, to determine the presence of biological activity on the item 1, the feedback component 66 includes at least one of: a visual camera or a chemical sensor. The visual camera can acquire visual data (e.g., visual, electronic, and/or the like) used to monitor the item 1, while the chemical sensor can acquire chemical data (e.g., chemical, electronic, and/or the like) used to monitor the item 1. For example, when the computer system 70 is operating the diffusive UV illuminator 10, the feedback component 66 monitoring the item 1 may be operated to detect the presence of microorganisms. In a specific embodiment, the visual camera comprises a fluorescent optical camera that can detect bacteria and/or viruses that become fluorescent under ultraviolet radiation. However, it is understood that a visual camera and a chemical sensor are only illustrative of various types of sensors that can be implemented. For example, the feedback component 66 can include one or more mechanical sensors (including piezoelectric sensors, various membranes, cantilevers, a micro-electromechanical sensor or MEMS, a nanomechanical sensor, and/or the like), which can be configured to acquire any of various types of data regarding the item 1.

The computer system 70 can be configured to control and adjust a direction, an intensity, a pattern, and/or a spectral power (e.g., wavelength) of the at least one ultraviolet radiation source within the illuminator 10, based on data acquired by the feedback component 66. The computer system 70 can control and adjust each property of the ultraviolet radiation source independently. For example, the computer system 70 can adjust the intensity, time duration, and/or time scheduling (e.g., including duration (e.g., exposure/illumination time)), duty cycle, time between exposures/illuminations, and/or the like) of the ultraviolet radiation source for a given wavelength. In a further embodiment, the feedback component 66 can include a sensor configured to evaluate an operating condition of the UV illuminator 10. To this extent, the UV illuminator 10 can include one or more surfaces, which is at least partially coated with a photoluminescent pigment. In this case, during and/or after operation of the UV illuminator 10, the feedback component 66 can sense (e.g., with a visual camera) whether the photoluminescent pigment is emitting visible light. In addition, the photoluminescent pigment can be configured to be visible external to the UV illuminator 10, in which case the pigment can provide an indication to the user 2 that the UV sources are operating. The computer system 70 can correlate an amount of visible light being emitted by the pigment with an operating condition of one or more of the ultraviolet sources in the UV illuminator 10. Each of the properties of the ultraviolet radiation source can be adjustable and controlled by the computer system 70 according to data provided by the feedback component 66.

For example, the computer system 70 can be configured to adjust the direction of the ultraviolet radiation according to a location of the biological activity detected on the item 1 by the feedback component 66 using any solution. The computer system 70 can be configured to utilize a target timing, intensity, and/or spectral power of the ultraviolet radiation according to a type of biological activity. That is, the sensing devices in the feedback component 66 can sense locations of higher levels of biological activity on the item 1, and the ultraviolet illuminator 10 can be configured by the computer system 70 to direct higher doses (by increasing intensity or exposure) of ultraviolet radiation at the locations with higher levels of biological activity (e.g., non-uniform ultraviolet radiation).

The feedback component 66 can also sense (via sensor and/or switch) that the item 1 is physically contained within the enclosure 64. In response to detection of the item 1 being located within the enclosure 64, the computer system 70 can be configured to automatically turn on the ultraviolet radiation. In one embodiment, the computer system 70 can be configured to set a periodic or an aperiodic schedule for the ultraviolet radiation when the item 1 is within the enclosure 64. This (periodic or aperiodic) schedule can be interrupted when the feedback component 66 senses that the item 1 is removed from the enclosure 64 and the computer system 70 can be configured to turn off the ultraviolet radiation. In this case, the schedule (periodic or aperiodic) can be resumed once the feedback component 66 senses the item 1 within the enclosure 64 again. The feedback component 64 can also sense that the enclosure 64 is open. In this example, the computer system 70 can be configured to turn off the ultraviolet radiation.

It is understood that the system 60 may include a power component 90 that is implemented separately from the item 1 to supply power to one or more of the various components of system 60, such as the UV illuminator 10, feedback component 66, computer system 70, and/or the like. For example, the item 1 may comprise a power source that is insufficient to operate the various devices of system 60 in addition to maintaining sufficient power to continue one or more aspects of the operation of the item 1. Regardless, the power component 90 can be utilized to operate system 60. The power component 90 can comprise any source of power including, but not limited to, a battery set, a solar cell, and/or the like. For example, the power component 90 can include any of various types of rechargeable batteries (e.g., lithium ion, nickel-cadmium, and/or the like). The power component 90 can be configured for operation of high efficiency direct current (DC) step-up/boost converters. In an embodiment, the power component 90 (e.g., conversion efficiency and maximum battery life) is configured (e.g., optimized) to keep a difference between the electrical power available versus the electrical power required for the various components at the minimum. In an embodiment, the power component comprises a battery set that is capable of being recharged through a typical household outlet. A charging system for this embodiment can comprise an electrical cord for charging that can include, for example, a cord with a Universal Serial Bus (USB) connection.

In an embodiment, the computer system 70 can implement multiple modes of operation depending on the source of power and/or an amount of power remaining. In particular, when a power component 90 of limited capacity is being utilized, one or more functions of system 60 can be disabled and/or reduced to lengthen an operating time for system 60. In another embodiment, a data-electrical link can be made between the item 1 and the enclosure 64 for data and/or power exchange between the item 1 and the computer system 70. For example, the item 1 and the enclosure 64 can be charged simultaneously via this data-electrical link. Additionally, the computer system 70 can provide data (via wireless and/or wired means) regarding the disinfection of the item 1 to the item 1, which can be presented to the user 2 (e.g., via an app installed on the item 1). In another embodiment, the power component 90 can comprise an electrical cord for charging the enclosure 64 via a household outlet.

While shown and described herein as a method and system for generating radiation, such as diffusive ultraviolet radiation for disinfecting an item, it is understood that aspects of the invention further provide various alternative embodiments. For example, in one embodiment, the invention provides a computer program fixed in at least one computer-readable medium, which when executed, enables a computer system to disinfect the item using a process described herein. To this extent, the computer-readable medium includes program code, such as the analysis program 80 (FIG. 10), which enables a computer system to implement some or all of a process described herein. It is understood that the term "computer-readable medium" comprises one or more of any type of tangible medium of expression, now known or later developed, from which a copy of the program code can be perceived, reproduced, or otherwise communicated by a computing device. For example, the computer-readable medium can comprise: one or more portable storage articles of manufacture; one or more memory/storage components of a computing device; paper; and/or the like.

In another embodiment, the invention provides a method of providing a copy of program code, such as the analysis program 80 (FIG. 10), which enables a computer system to implement some or all of a process described herein. In this case, a computer system can process a copy of the program code to generate and transmit, for reception at a second, distinct location, a set of data signals that has one or more of its characteristics set and/or changed in such a manner as to encode a copy of the program code in the set of data signals. Similarly, an embodiment of the invention provides a method of acquiring a copy of the program code, which includes a computer system receiving the set of data signals described herein, and translating the set of data signals into a copy of the computer program fixed in at least one computer-readable medium. In either case, the set of data signals can be transmitted/received using any type of communications link.

In still another embodiment, the invention provides a method of generating a system for disinfecting an item. In this case, the generating can include configuring a computer system, such as the computer system 70 (FIG. 10), to implement a method of disinfecting the item as described herein. The configuring can include obtaining (e.g., creating, maintaining, purchasing, modifying, using, making available, etc.) one or more hardware components, with or without one or more software modules, and setting up the components and/or modules to implement a process described herein. To this extent, the configuring can include deploying one or more components to the computer system, which can comprise one or more of: (1) installing program code on a computing device; (2) adding one or more computing and/or I/O devices to the computer system; (3) incorporating and/or modifying the computer system to enable it to perform a process described herein; and/or the like.

The foregoing description of various aspects of the invention has been presented for purposes of illustration and description. It is not intended to be exhaustive or to limit the invention to the precise form disclosed, and obviously, many modifications and variations are possible. Such modifications and variations that may be apparent to an individual in the art are included within the scope of the invention as defined by the accompanying claims.

What is claimed is:

1. A diffusive illuminator comprising:
   a set of light sources;
   a light guiding structure including a plurality of layers, wherein the light guiding structure includes a plurality of layers at least partially formed of a fluoropolymer and at least one layer formed of a transparent fluid, and wherein the light guiding structure guides light emitted by the set of light sources and includes an emission surface through which diffused light exits; and
   a plurality of diffusive elements associated with at least one of the plurality of layers, wherein each of the plurality of diffusive elements diffusively reflects and/or transmits the light, and wherein the plurality of diffusive elements are arranged to provide a predetermined uniformity of the diffused light at a predetermined target distance corresponding to a surface to be illuminated.

2. The diffusive illuminator of claim 1, wherein the plurality of diffusive elements includes a plurality of diffusive elements formed on a surface of at least one of the plurality of layers.

3. The diffusive illuminator of claim 1, wherein the plurality of diffusive elements includes a plurality of diffusive elements located within the light guiding structure.

4. The diffusive illuminator of claim 3, wherein the light guiding structure includes:
   a first layer filled with a transparent fluid through which a majority of the light is guided; and
   a second layer filled with a transparent fluid, wherein the second layer includes the plurality of diffusive elements.

5. The diffusive illuminator of claim 1, wherein the set of light sources comprises a set of ultraviolet radiation emitters.

6. The diffusive illuminator of claim 5, wherein the set of ultraviolet radiation emitters includes a set of ultraviolet light emitting diodes.

7. The diffusive illuminator of claim 5, wherein the set of ultraviolet radiation emitters are coupled to the light guiding structure using an ultraviolet transparent material.

8. The diffusive illuminator of claim 5, wherein the set of light sources further comprises a set of visible light sources.

9. The diffusive illuminator of claim 1, wherein the set of light sources include a reflector for at least partially collimating the light.

10. The diffusive illuminator of claim 1, wherein the light guiding structure is configured to at least partially collimate the light.

11. A system comprising:
    a diffusive illuminator including:
      a set of light sources;
      a light guiding structure including a plurality of layers, wherein the light guiding structure includes a plurality of layers at least partially formed of a fluoropolymer and at least one layer formed of a transparent fluid, and wherein the light guiding structure guides light emitted by the set of light sources and includes an emission surface through which diffused light exits; and a plurality of diffusive elements associated with at least one of the plurality of layers, wherein each of the plurality of diffusive elements diffuses the light, and wherein the plurality of diffusive elements are arranged to provide a predetermined angular distribution of intensity of the diffused light at a predetermined target distance corresponding to a surface to be illuminated; and means for adjusting the plurality of diffusive elements based on at least one attribute of the predetermined angular distribution of intensity.

12. The system of claim 11, wherein the plurality of diffusive elements includes a plurality of diffusive elements located within at least one of the at least one layer formed of a transparent fluid.

13. The system of claim 11, wherein the means for adjusting includes:

a plurality of magnets located adjacent to a back surface of the light guiding structure;

a sensing device configured to acquire data regarding the diffused light; and a control system configured to adjust at least one of: a location or a strength of each of the plurality of magnets based on the diffused light.

14. The system of claim 13, wherein the control system adjusts the at least one of: the location or the strength using a genetic algorithm for optimizing a distribution of the diffused light.

15. The system of claim 11, wherein at least some of the plurality of diffusive elements diffusively reflects the light.

16. A disinfection system comprising:
a diffusive illuminator including:
a set of ultraviolet light sources;
a light guiding structure including a plurality of layers, wherein the light guiding structure includes a plurality of layers at least partially formed of a fluoropolymer and at least one layer at least partially formed of an ultraviolet transparent fluid, and wherein the light guiding structure guides light emitted by the set of ultraviolet light sources and includes an emission surface through which diffused ultraviolet light exits; and
a plurality of diffusive elements associated with at least one of the plurality of layers, wherein each of the plurality of diffusive elements diffuses the ultraviolet light, and wherein the plurality of diffusive elements are arranged to provide a predetermined uniformity of the diffused ultraviolet light at a predetermined target distance corresponding to a surface to be illuminated; and
a control system configured to operate the set of ultraviolet light sources to illuminate an item using the diffused ultraviolet light.

17. The system of claim 16, at least some of the plurality of diffusive elements diffusively reflects the ultraviolet light.

18. The system of claim 16, wherein the control system is further configured to adjust the plurality of diffusive elements based on at least one attribute of the diffused light.

19. The system of claim 16, wherein the set of ultraviolet light sources are coupled to the light guiding structure using an ultraviolet transparent material.

20. The system of claim 16, wherein at least a first region of at least one of the at least one layer formed of a transparent fluid has a variable diameter in a direction away from the set of light sources.

* * * * *